US010786397B2

(12) United States Patent
Norton (10) Patent No.: US 10,786,397 B2
(45) Date of Patent: Sep. 29, 2020

(54) THERAPEUTIC COMPRESSION DEVICE AND METHOD

(71) Applicant: Steven Norton, Fair Haven, NJ (US)

(72) Inventor: Steven Norton, Fair Haven, NJ (US)

(73) Assignee: Norton Salas Group, Inc., Matawan, NJ (US)

( * ) Notice: Subject to any disclaimer, the term of this patent is extended or adjusted under 35 U.S.C. 154(b) by 958 days.

(21) Appl. No.: 15/379,702

(22) Filed: Dec. 15, 2016

(65) Prior Publication Data

US 2017/0095392 A1  Apr. 6, 2017

Related U.S. Application Data

(63) Continuation-in-part of application No. 13/193,225, filed on Jul. 28, 2011, now Pat. No. 10,166,150.

(51) Int. Cl.
*A61F 13/08* (2006.01)
*B32B 27/06* (2006.01)
(Continued)

(52) U.S. Cl.
CPC .............. *A61F 13/08* (2013.01); *A61H 7/001* (2013.01); *B32B 3/02* (2013.01); *B32B 3/08* (2013.01); *B32B 3/10* (2013.01); *B32B 5/18* (2013.01); *B32B 7/12* (2013.01); *B32B 15/046* (2013.01); *B32B 15/095* (2013.01); *B32B 27/065* (2013.01); *B32B 27/08* (2013.01); *B32B 27/28* (2013.01); *B32B 27/302* (2013.01); *B32B 27/34* (2013.01); *B32B 27/36* (2013.01); *A61H 2201/1635* (2013.01); *A61H 2205/065* (2013.01); *B32B 2250/04* (2013.01); *B32B 2250/05* (2013.01); *B32B 2266/025* (2013.01);
(Continued)

(58) Field of Classification Search
CPC .... A61H 2201/1645; A61H 2201/1635; A61H 7/001; A61H 2011/005; A61H 2205/065; A61F 13/08; A61F 13/085; A61F 13/104; A61F 13/107; A61F 5/0118; A61F 5/013; A61F 5/05866; A41D 19/01582; A41D 19/01588; A43B 5/0447; A43C 11/16; A43C 11/165
USPC ...................................... 2/16–21; 602/20, 21
See application file for complete search history.

(56) References Cited

U.S. PATENT DOCUMENTS

4,676,233 A  6/1987 Scheinberg
4,899,763 A * 2/1990 Sebastian .............. A61F 5/0118
128/878
(Continued)

*Primary Examiner* — Colin W Stuart
*Assistant Examiner* — Douglas Y Sul
(74) *Attorney, Agent, or Firm* — Thomas L. Adams (57) ABSTRACT

A compression device can treat edema with a plurality of shell structures, each having an inside pad. A ligature network is routed across the shell structures. A plurality of tensioners mounted on at least some of the plurality of shells can separately adjust tension in different portions of the ligature network to affect the balance of compression forces at spaced positions along the plurality of padded shells. At least some of the shell structures have an underpass sized to accommodate passage of a portion of the ligature network. The underpass is integral with a corresponding one of the plurality of shell structures. In one case the shells include an interconnected plurality of volar shells placed on one side of a body part and a dorsal shell on the opposite side.

33 Claims, 8 Drawing Sheets

(51) Int. Cl.
*B32B 3/10* (2006.01)
*B32B 7/12* (2006.01)
*B32B 3/02* (2006.01)
*B32B 5/18* (2006.01)
*B32B 3/08* (2006.01)
*B32B 27/08* (2006.01)
*A61H 7/00* (2006.01)
*B32B 15/04* (2006.01)
*B32B 15/095* (2006.01)
*B32B 27/34* (2006.01)
*B32B 27/28* (2006.01)
*B32B 27/30* (2006.01)
*B32B 27/36* (2006.01)

(52) U.S. Cl.
CPC ............ *B32B 2266/0221* (2013.01); *B32B 2266/0278* (2013.01); *B32B 2266/06* (2013.01); *B32B 2307/732* (2013.01); *B32B 2437/02* (2013.01); *B32B 2535/00* (2013.01)

(56) References Cited

U.S. PATENT DOCUMENTS

| | | |
|---|---|---|
| 5,152,302 A | 10/1992 | Fareed |
| 5,713,837 A * | 2/1998 | Grim ................... A61F 5/0111 602/21 |
| 6,526,592 B1 | 3/2003 | Best |
| 6,785,909 B1 | 9/2004 | Li |
| 6,991,612 B2 | 1/2006 | Scheinberg et al. |
| 7,135,005 B2 | 11/2006 | Kania |
| 2005/0066412 A1 | 3/2005 | Morrow |
| 2006/0135902 A1 | 6/2006 | Ingimundarson et al. |
| 2006/0156517 A1 * | 7/2006 | Hammerslag ........ A43C 11/00 24/68 SK |
| 2007/0100266 A1 * | 5/2007 | Hargrave ............ A61F 5/0118 602/21 |
| 2008/0228117 A1 | 9/2008 | Fareed |
| 2010/0056973 A1 * | 3/2010 | Farrow ................ A61F 13/08 602/63 |
| 2010/0331748 A1 * | 12/2010 | Nordt, III ............ A61F 5/022 602/20 |
| 2012/0004587 A1 * | 1/2012 | Nickel ................. A61F 5/0118 602/21 |
| 2012/0010547 A1 * | 1/2012 | Hinds ................. A61F 5/0118 602/21 |
| 2012/0316485 A1 * | 12/2012 | Fryda ................. A61F 5/0118 602/21 |
| 2013/0245522 A1 * | 9/2013 | Modglin ............... A61F 5/01 602/16 |
| 2014/0276274 A1 * | 9/2014 | Clare .................. A61H 1/008 601/84 |
| 2015/0150705 A1 * | 6/2015 | Capra ................... A61F 5/01 602/6 |

* cited by examiner

THERAPEUTIC COMPRESSION DEVICE AND METHOD

CROSS-REFERENCES TO RELATED APPLICATIONS

This application claims the benefit of U.S. patent application Ser. No. 13/193,225, filed Jul. 28, 2011, the contents of which are hereby incorporated by reference herein.

BACKGROUND OF THE INVENTION

1. Field of the Invention

The present invention relates to devices and methods for treating a patient with compression, and in particular, to techniques employing separate shells.

2. Description of Related Art

Edema is a medical condition that requires careful treatment. Lymphedema, a type of edema, is a swelling of a body part, often the result of the abnormal accumulation in the affected area of protein-rich edema fluid (primarily lymph fluids). Lymphedema is classified as either primary or secondary. Primary lymphedema is the result of lymphatic dysplasia. It may be present at birth but more often develops later in life without obvious cause. Secondary lymphedema is much more common and is the result of surgery or is a side effect of radiation therapy for cancer. Secondary forms may also occur after injury, scarring, trauma, or infection of the lymphatic system. Lymphedema treatment options offered in the United States include surgery, medication, pneumatic compression pump therapy, Manual Lymph Drainage (MLD), and Complete Decongestive Therapy (CDT).

Surgery and medication have their place, but their success is not guaranteed and comes with risks. The pneumatic compression pump is a mechanical device that "milks" the lymph fluid out of the swollen extremity. The problems with pneumatic pumps are numerous and any results achieved are usually very temporary.

Lymphedema physical therapy treatment would not be possible without compression therapy employing bandages and elastic compression garments. Elastic compression garments are easily used and sold under the trade names. Solaris, JoviPak, CircAid, Biacare, and Reid Sleeve. Another compression therapy involves bandaging with short stretch bandages and is a highly skilled procedure designed to take advantage of natural pumping pressures.

Lymph is propelled through the various lymph vessels by muscular activity, breathing, etc. Bandaging/garments improve the efficiency of the muscle and joint pump and also prevents the re-accumulation of evacuated lymph fluid. These techniques will also break up deposits of accumulated scar and connective tissue.

The nature of compression varies greatly when a comparison is made between short stretch bandages and elastic compression garments. Both are necessary complements to a program of Complete Decongestive Therapy (CDT) when utilized by competent and well-trained therapists. The distinction lies in the working and resting forces generated by these two forms of compression. Elastic compression garments are designed to provide a pressure gradient favoring proximal fluid flow and are comfortable and convenient. However, they tend to produce constant resting pressure without enhanced working pressure. Short stretch compression bandages supports a limb without constant "squeezing" (i.e. will exhibit low resting pressure), but when a limb is exercised produces relatively high working pressure.

No effective homecare device exists to maintain/reduce lymphedema/edema consistent with the principles of CDT (Complete Decongestive Therapy). Therefore, patients are saddled with the responsibility of life-long lymphedema control, but the task is arduous, tedious and time consuming. When self-applied compression is performed with less than sufficient skill, it can also be painful, counter-therapeutic or even damage the limbs' health.

Aftermarket compression products have tried alternative solutions to replace multilayered compression bandages. Treatment at joints is most problematical for these products. Even at the limb segments (between joints) the solutions offered utilize unsatisfactory materials and tensioning techniques to generate pressure. As a result these products lack continuous working pressure (cast-like containment) longitudinally as well as structure to prevent buckling and bulging of tissues.

See also U.S. Pat. Nos. 4,676,233; 5,152,302; 6,526,592; 6,785,905; 7,135,005; and 6,991,612; as well as US Patent Application Publication Nos. 2005/0066412; 2006/0135902; 2007/0100266; and 2008/0228117.

SUMMARY OF THE INVENTION

In accordance with the illustrative embodiments demonstrating features and advantages of the present invention, there is provided a compression device for treating edema. The device includes a plurality of shell structures. A plurality of inside pads underlie the shell structures. The device also includes a ligature network routed across the plurality of shell structures. The network includes a plurality of tensioners mounted on at least some of the plurality of shell structures. The plurality of tensioners are operable to separately adjust tension in different portions of the ligature network. At least some of the plurality of shell structures have at least one underpass sized to accommodate passage of a portion of the ligature network. The at least one underpass is integral with a corresponding one of the plurality of shell structures.

In accordance with another aspect of the invention, there is provided a compression device for treating edema. The device includes a plurality of shell structures, and a plurality of inside pads underlying the shell structures. The device also includes a ligature network routed across the plurality of shell structures. The network includes a plurality of tensioners mounted on at least some of the plurality of shell structures. The plurality of tensioners are operable to separately adjust tension in different portions of the ligature network One of the plurality of shell structures includes a plurality of panels having at least one coupling device connecting together at least a coupled pair of the plurality of panels.

In accordance with yet another aspect of the invention, there is provided a compression device for treating edema. The device includes a plurality of shell structures. The plurality of shells include a dorsal shell and an adjacent plurality of volar shells. Also included is a plurality of inside pads underlying the shell structures. The device also includes a ligature network routed across the plurality of shell structures. The ligature network includes a plurality of tensioners mounted on at least some of the plurality of shell structures.

In accordance with still yet another aspect of the invention, a method is provided for treating edema in a body part with a ligature network and a plurality of padded shells. The plurality of padded shells include a dorsal shell and a plurality of interconnected volar shells. The method includes the step of routing the ligature network across the plurality of shells. The method also includes the step of placing the plurality of volar shells on one side of the body part and the dorsal shell on the opposite side. In another step, with the body part embraced by the padded shells, tension in different portions of the ligature network is separately adjusted to affect the balance of compression forces at spaced positions along the plurality of padded shells.

By employing devices and methods of the foregoing type an improved technique is achieved for treating edema. For example, lymphedema limb areas need not be immobilized and the present device does not function as a cast or an immobilizer. Areas of joint articulation can sustain movement without abrasion or discomfort. The natural muscle and joint pumps will be allowed to activate a natural fluid pumping effect. Allowing movement within a compression device tends to reverse lymphostatic fibrosis.

A disclosed embodiment is presented for treating the hand, although treatment of other body parts is described. The embodiment for treating the hand employs a number of padded shells, one placed on the dorsum and three others placed on the palm. The three palmar shells include a transverse shell placed at the knuckles (metacarpophalangeal joints). This transverse shell has, running from right to left, a sinuous curve that tends to flatten these knuckles. This avoids cupping that would tend to apply excessive stress to the region.

The other two palmar shells are located side by side, below the transverse shell, i.e., closer to the wrist. One of these shells is located medially (closer to the thumb) and the other is located laterally (further from the thumb). The adjacent edges of these two shells (medial and lateral shells) are curved inwardly to accommodate the natural curvature or cupping in the center of the palm.

In order to achieve an appropriate pressure, a disclosed ligature network is formed from a number of cords that are routed across the padded shells to produce a desired effect. In particular, these cords are routed through guides strategically placed at various locations on the opposing shells A disclosed network has two circuits that are independently tightened by two tensioners. The disclosed tensioners are cord winders placed in strategic locations on one or more of the shells.

In this disclosed embodiment the ligature network is constrained by a number of guides on the various padded shells. The guides can be integrally molded as part of the plastic of the outer shell. The disclosed guides have a number of open channels alternating with underpasses, which underpasses are closed on top and open on the bottom. In some cases an end of these guides terminate in a concave gutter that leads to the edge of the shell where the cord can jump from one side of the treated hand to the other. In a disclosed embodiment, this gutter is actually formed as three gutters diverging from a common point, allowing the user to select one of the three that is best suited to the hand being treated.

In this embodiment a pair of manually operable winders on the dorsal shell each have an incoming pair of cord ends that can be drawn inwardly to shorten the length of a loop of cord that is passing over designated shells. In this case one of the winders adjusts the tension in a loop of cord that runs between the dorsal shell and the transverse shell on the palmar side. The other winder adjusts the tension in a loop that runs between the dorsal shell, and the medial and lateral shells.

The disclosed dorsal shell connects to the volar shells solely by means of the ligature network. On the other hand, the volar shells connect to each other by means of a coupling device. In one case the coupler is a number of flexible splines that connect between respective pairs of the volar shells. In another case the coupler is a complex substrate that is composed of three interconnected regions, one for each of the volar shells. This substrate can be molded as a single element with the three regions connected by flexible bridges.

These padded shells are fashioned to accommodate the specific body part being treated. For example, an outline of a hand may be applied to plastic panels, which may be appropriately notched to allow articulation of the thumb.

All of these padded shells include a plastic panel that is relatively stiff, so that the shells can apply transaxial pressure without squeezing the hand laterally. This arrangement cancels out high lateral pressures, and accentuates high dorsal and palmar pressures.

Lymphedema is a staged condition according to disease severity (stages 1, 2, 3). As such it requires modifications in the approach according to the quantity of swelling and tissue integrity. The above noted shells apply the external force, but inner-padding materials will be tailored to modify the force according to the disease severity, desired gradient of pressure, limb girth and abnormal contours if any.

With this in mind, the inside of the disclosed panels will be fitted with pads; for example, one or more layers of foam material. In one embodiment the layer next to the plastic panel is relatively dense and readily accommodates transaxial force, while the layer closest to skin tissue is an open cell foam that conforms more closely to the curves of the hand and increases comfort.

Proper treatment requires that skin integrity be preserved to combat any localized immune deficiency. To address this requirement the shells' pads ought to be hypoallergenic, customized to the patient, and hygienic.

Lymphedema treatment requires that a gradient of pressure be exerted regardless of the contour of the swollen limb. Pressure applied to hypothetical conical shapes will respond according to the "law of Laplace" ($P=Tc/R$), however swollen limbs are not always conical. To address this anatomical requirement "zones" of pressure are created and padding modified suitably to direct fluid from distal areas towards proximal areas. Limbs that have received treatment in the clinic (e.g., with CDT) become more normally shaped (from columnar to conical again) and readily responsive to the above compression device.

Devices of this type may be used as an adjunct to, or a follow-up after, professional therapy. Also, after the initial fitting of the device, a user will be able to readily remove the device and later place it back on the body part under treatment without the need for professional assistance. In addition, since the tension in the ligature network is readily adjusted, a user can easily adjust tension throughout the day as needed.

Devices according to the foregoing principles can achieve high working pressure, and low resting pressure throughout. Such devices are adaptable to the edema reduction process by allowing movement, and normal activity. In the disclosed embodiment, tension is easily adjusted so a user is able to regularly conduct subtle re-tensioning.

BRIEF DESCRIPTION OF THE DRAWINGS

The above brief description as well as other objects, features and advantages of the present invention will be more fully appreciated by reference to the following detailed description of illustrative embodiments in accordance with the present invention when taken in conjunction with the accompanying drawings, wherein.

DETAILED DESCRIPTION

Figure 1:
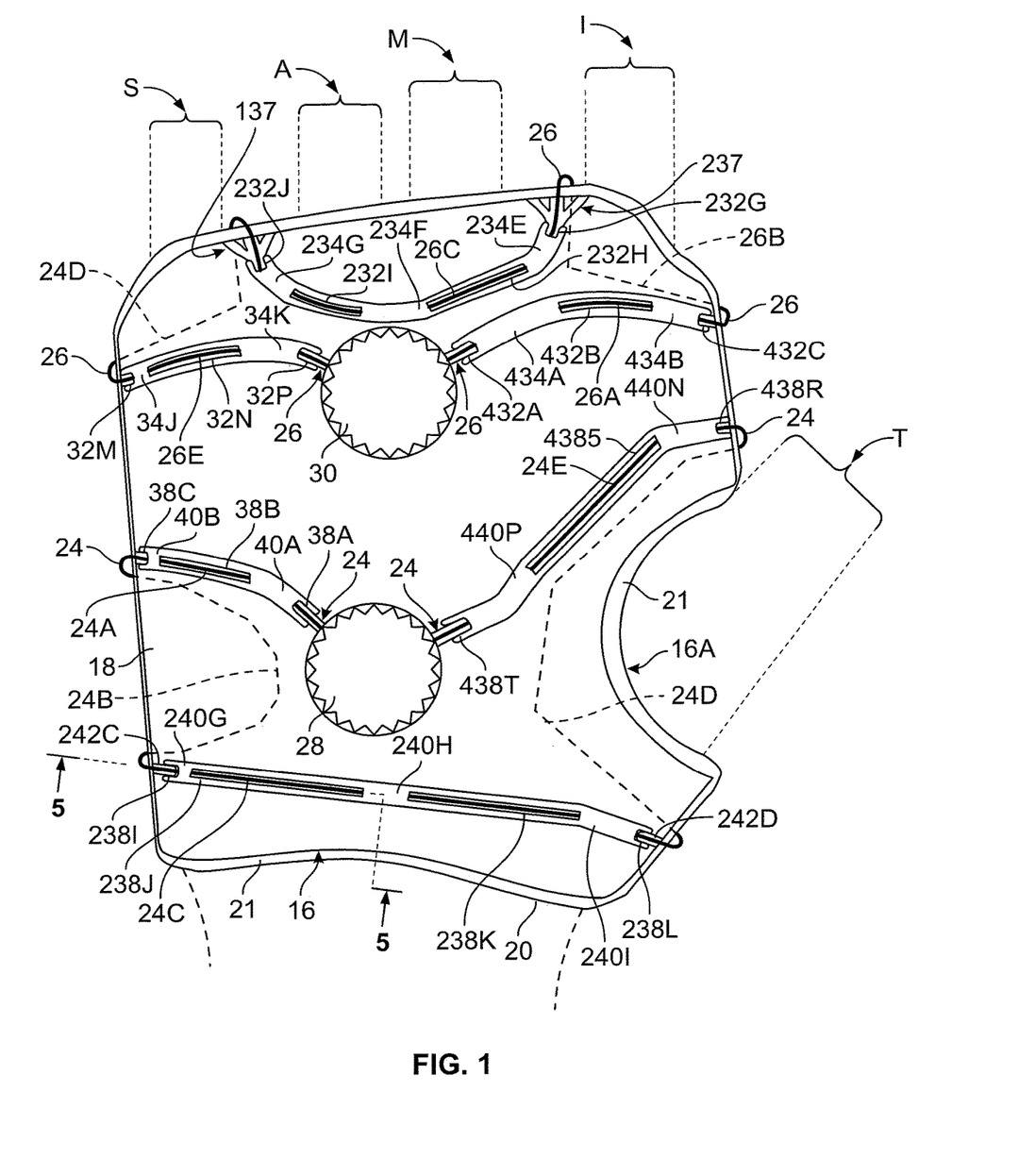
FIG. 1 is an outside view of a dorsal shell that is part of a compression device in accordance with principles of the present invention.
Figure 2:
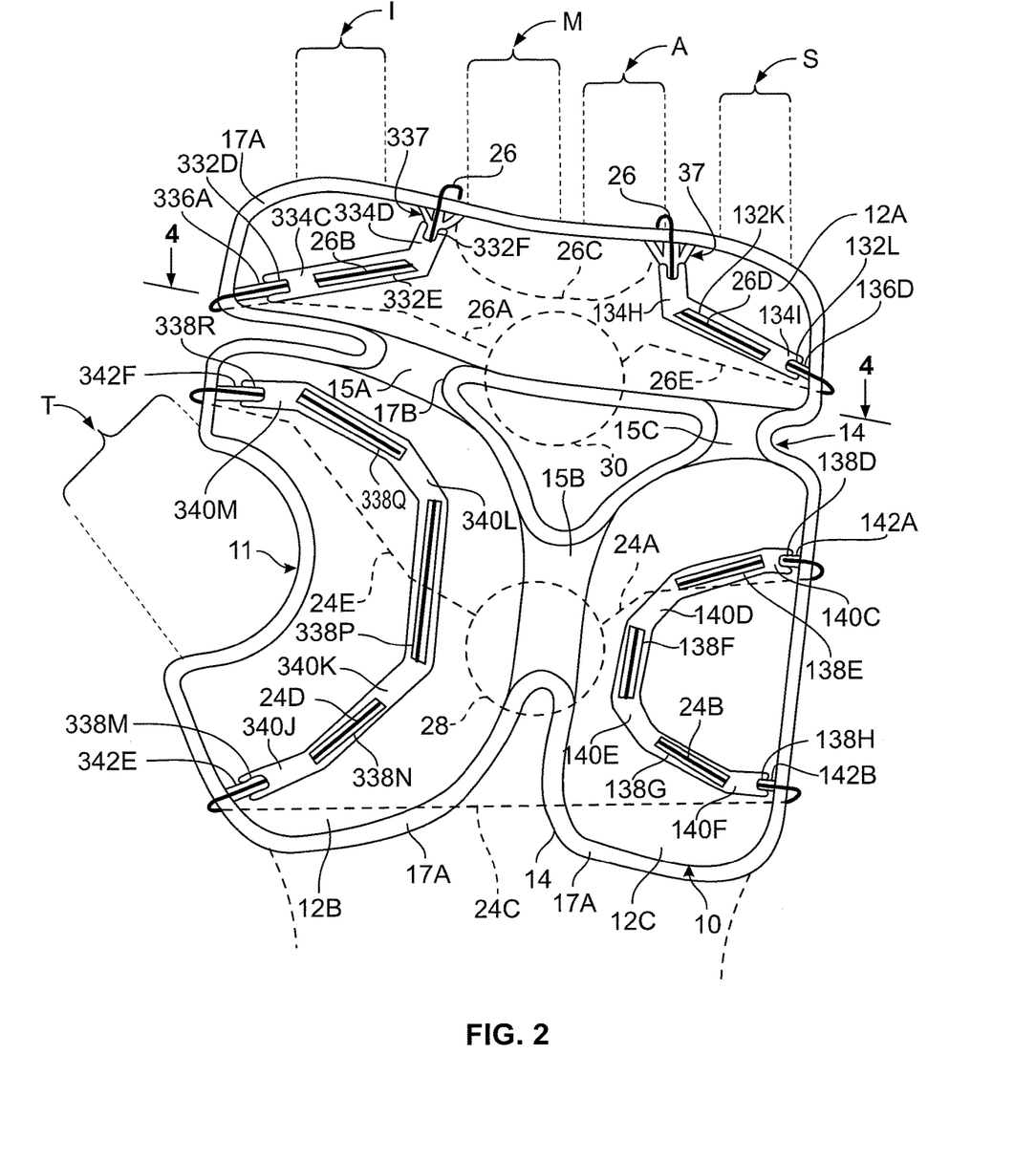
FIG. 2 is an outside view of a trio of volar shells cooperating with the dorsal shell of the compression device of FIG. 1.

Referring to FIGS. 1-7, the illustrated compression device has dorsal shell structure 16 (FIG. 1) and volar shell structure 10 (FIG. 2). Dorsal shell structure 16 has shell 18 (also referred to as panel 18) lying between surrounding walls 21 of inside pad 20. This embodiment is designed for the left hand, although designing for a right hand will be apparent.

FIG. 1 shows the outline of dorsal shell panel 18, it being understood that the right and left edges are rolled approximately 45°, except at the curved notch 16A provided for thumb T. Notch 16A allows articulation at the thumb joint. Overall, dorsal shell structure 16 can be given an appropriate curve to accommodate the natural curves of the human hand. The dorsal shell structure 16 can be provided in a number of standard sizes to accommodate hands of various sizes.

In FIG. 2 volar shell structure 10 includes three panels including a transverse volar shell 12A, a medial volar shell 12B, and a lateral volar shell 10C, respectively. The right and left edges of volar shell structure 10 are again rolled approximately 45°, except in the vicinity of curved notch 11, which is provided for thumb T and allows articulation at the thumb joint. The adjoining portions of shells 12B and 12C are curved inwardly (toward the dorsal shell of FIG. 1) to accommodate the natural cupping of the palm. Shells 12B and 12C are located between the wrist joint and the transverse proximal edge of shell 12A.

Shell panels 18, 12A, 12B, and 12C of FIGS. 1 and 2 may be made of a molded thermoplastic (injection molded, blow molded, or vacuum molded). Suitable materials include PET, PETG, Nylon 6, Nylon 66, or ABS, although other embodiments may employ various synthetic materials, sheet metals, composite materials, or other materials that are shaped by stamping, etching, forging, etc. Shell panels 18, 12A, 12B, and 12C are designed to be relatively stiff in order to transmit compression forces normal to their surfaces.

Figure 3:
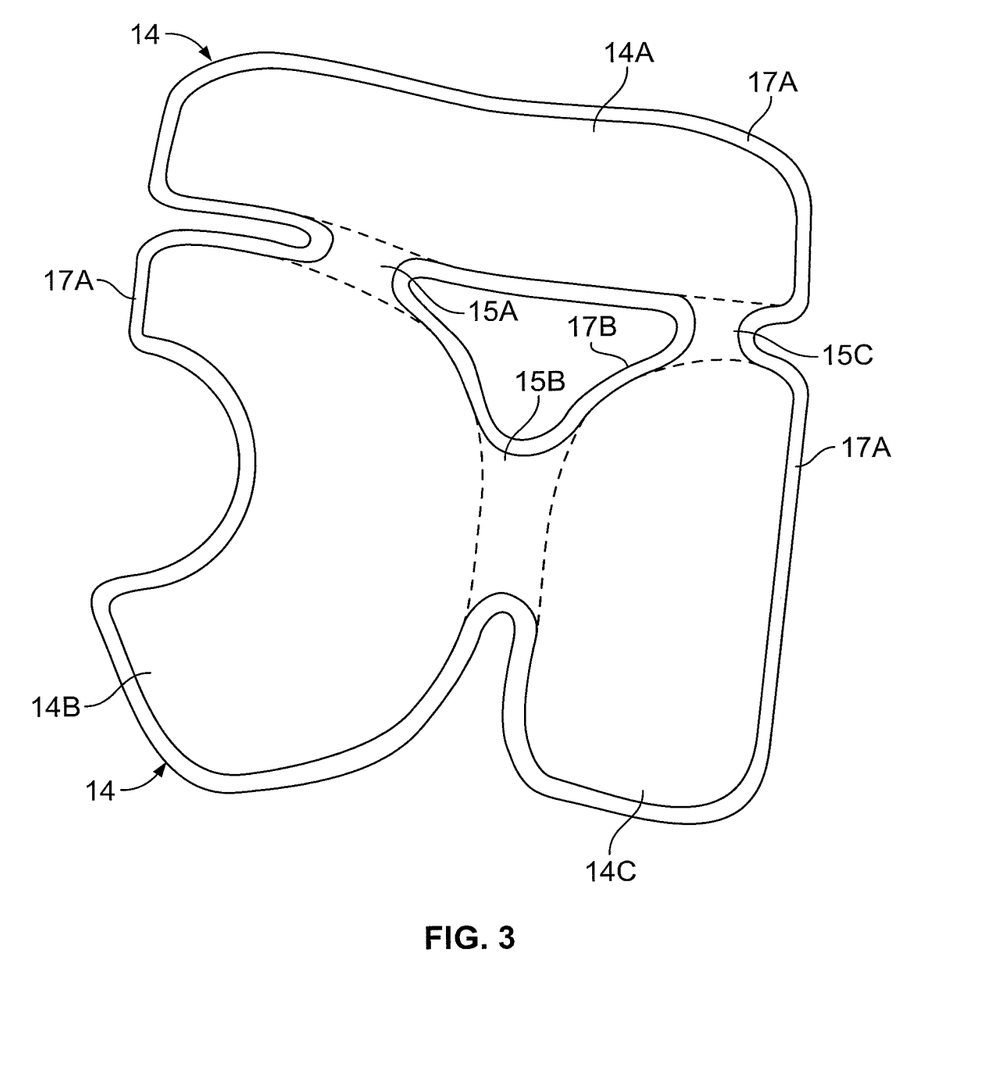
FIG. 3 is an outside view of the pad of FIG. 2.
Figure 4:
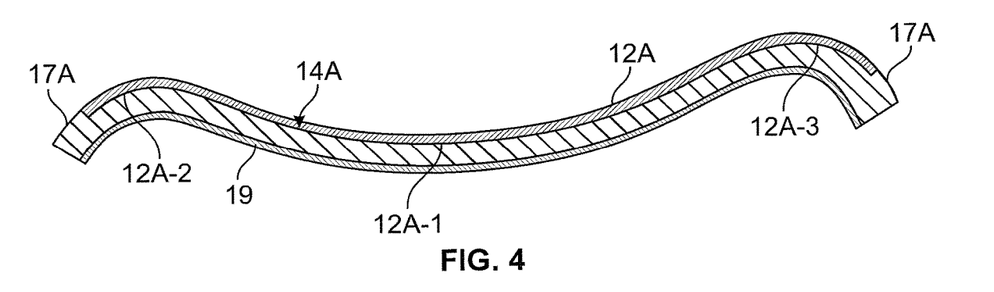
FIG. 4 is a sectional view of one of the padded shells taken along line 4-4 of FIG. 2.

In FIGS. 2, 3 and 4 volar panels 12A, 12B, and 12C are interconnected by means of inside pad 14, specifically its bridges 15A, 15B, and 15C acting as coupling devices. In FIG. 3 inside pad 14 is shown as a collection of three pads, namely inside pads 14A, 14B, and 14C sized to receive shell panels 12A, 12B, and 12C of FIG. 2, respectively. In particular, panels 12A, 12B, and 12C are positioned between walls 17A and 17B before being glued in place. (Pads 14A, 14B, and 14C are also referred to as three strata of a substrate.)

Flexible bridges 15A and 15C of FIG. 3 allow pad region 14A and thus shell 12A to articulate relative to the other two pad regions 14B and 14C (and their respective shells 12B and 12C). Flexible bridge 15B allows articulation between pad regions 14B and 14C, and therefore articulation between shells 12B and 12C. Bridges 15A, 15B, and 15C are coplanar with pad regions 14A, 14B, and 14C, and allow them to act as three coupled pairs of articulating strata. (Inside pads 14A, 14B, and 14C are also referred to as a predetermined set of inside pads.)

FIG. 4 shows the sinuous shape of volar shell 12A whose inside surface lies against pad region 14A of inside pad 14. In this view, inside pad 14A is shown bordered by walls 17A. The inside surface of shell 12A has a central region with a convex central interval 12A-1, and is bordered on the right and left by a transversely spaced pair of concave intervals 12A-2 and 12A-3.

In FIG. 4 the surface of pad region 14A facing the skin is fitted with a sheet of hook and loop material 19. In fact, sheet 19 is coterminous with the three sectors of inside pad 14 (FIG. 3) and thus underlies elements 14A, 14B, 140, 15A, 15B, 15C, 17A and 17B.

Referring again to FIG. 1, inside pad 20 has a structure similar to pad 14 of FIG. 3, except pad 20 is designed to accommodate a single shell panel 18. For this reason, pad 20 has a single surrounding wall 21 with an inside perimeter matching the outline of shell panel 18. The underside of pad 20 is covered with hook and loop material (not shown), in a fashion similar to the other inside pad (pad 14 of FIGS. 2-4).

Referring to FIGS. 1 and 2, padded shell arrangements 16/20 and 10/14 are pressed together with a ligature network employing nylon cords arranged in a pair of circuits 24 and 26 Circuit 24 terminates at network tensioner 28, while circuit 26 terminates at network tensioner 30.

Tensioner 28 is a manually operable winder that can be rotated clockwise (counterclockwise) to wind (unwind) cord segment 24A relative to a reel (not shown) inside the tensioner. Cord segment 24E will not be wound although winding may be implemented in other embodiments. Tensioner 30 is a manually operable winder that can be rotated clockwise (counterclockwise) to wind (unwind) cord segments 26E relative to a reel (not shown) inside the tensioner.

In this embodiment tensioners 28 and 30 are identical, but need not be so. Winders of this type can be obtained from Boa Technology, Inc. of Steamboat Springs, Colo.

In FIG. 1 circuit 24 has cord segment 24A running from winder 28 atop shell 18 through channel 38A, underpass 40A, channel 38B, underpass 40B and channel 38C. The structure of these channels and underpasses will be described in further detail presently. Cord segment 24A traverses the edge of shell 18 and crosses over to run atop shell 12C, that departed segment being shown in phantom as cord segment 24B.

In FIG. 2 cord segment 24B is threaded through gutter 142A, channel 138D, underpass 140C, channel 138E, underpass 140D, channel 138F, underpass 140E, channel 138G, underpass 140F, channel 138H, and gutter 142B. Cord segment 24B traverses the edge of shell 12C and crosses over to run atop shell 18, that departed segment being shown in phantom as cord segment 24C.

In FIG. 1 cord segment 24C is threaded through gutter 242C, channel 238I, underpass 240G, channel 238J, underpass 240H, channel 238K, underpass 240I, channel 238L, and gutter 242D. Cord segment 24C traverses the edge of shell 18 and crosses over to run atop shell 12B, that departed segment being shown in phantom as cord segment 24D.

In FIG. 2 cord segment 24D is threaded through gutter 342E, channel 338M, underpass 340J, channel 338N, underpass 340K, channel 338P, underpass 340L, channel 338Q, underpass 340M, channel 338R, and gutter 342F. Cord segment 24D traverses the edge of shell 12B and crosses over to run atop shell 18, that departed segment being shown in phantom as cord segment 24E.

In FIG. 1 cord segment 24E is threaded through channel 438R, underpass 440N, channel 438S, underpass 440P, and channel 438T, before returning to winder 28.

Referring now to circuit 26, in FIG. 1 cord segment 26A runs from winder 30 atop shell 18 through channel 432A, underpass 434A, channel 432B, underpass 434B and channel 432C. Cord segment 26A traverses the edge of shell 18 and crosses over to run atop shell 12A, that departed segment being shown in phantom as cord segment 26B.

In FIG. 2 cord segment 26B is threaded through gutter 336A, channel 332D, underpass 334C, channel 332E, underpass 334D, channel 332F to a diverging trio of gutters 337. Cord 26 is shown traveling through the center one of the trio of gutters 337, but one of the other paths can be chosen if it provides a more comfortable route between fingers I and M. Cord segment 24B traverses the edge of shell 12A and crosses over to run atop shell 18, that departed segment being shown in phantom as cord segment 24C.

In FIG. 1 cord segment 26C travels through the center one of a diverging trio of gutters 237, but one of the other paths can be chosen if it provides a more comfortable route between fingers I and M. From there, cord segment 26C travels through channel 232G, underpass 234E, channel 232H, underpass 234F, channel 232I, and underpass 232G to the center one of a diverging trio of gutters 137. The chosen one of the trio will be chosen to optimize the comfort when passing between fingers A and S. Cord 26 traverses the edge of shell 18 and crosses over to run atop shell 12A, that departed segment being shown in phantom as cord segment 24D.

In FIG. 2 cord segment 26D travels through the center one of a diverging trio of gutters 37 (one of them chosen for best comfort). From there cord segment 26D is threaded through underpass 134H, channel 132K, underpass 134I, and channel 132L to gutter 136D. Cord segment 24D traverses the edge of shell 12A and crosses over to run atop shell 18, that departed segment being shown in phantom as cord segment 24E.

In FIG. 1 cord segment 26E is threaded through channel 32M, underpass 34J, channel 32N, underpass 34K, and channel 32P, before returning to winder 30.

Figure 5:
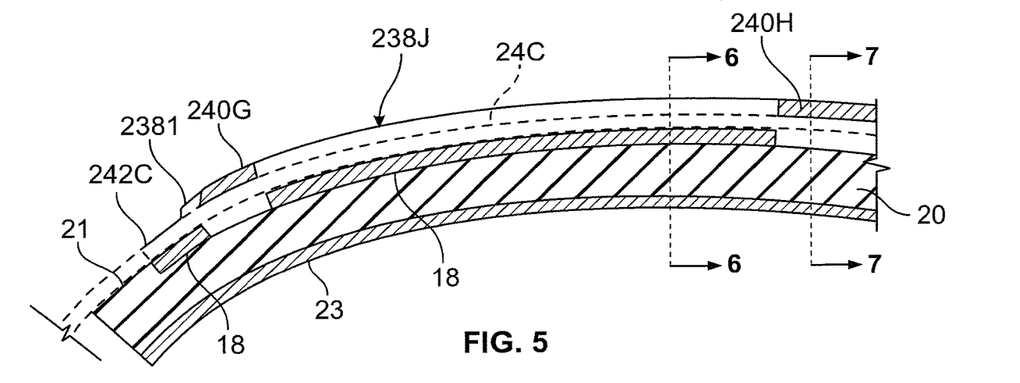
FIG. 5 is a sectional view of a fragment of one of the padded shells taken along line 5-5 of FIG. 1.
Figure 6:
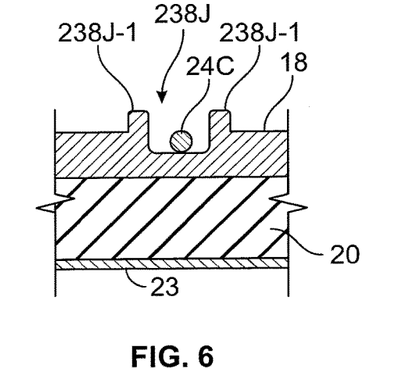
FIG. 6 is a sectional view of one of the padded shells taken along line 6-6 of FIG. 5.
Figure 7:
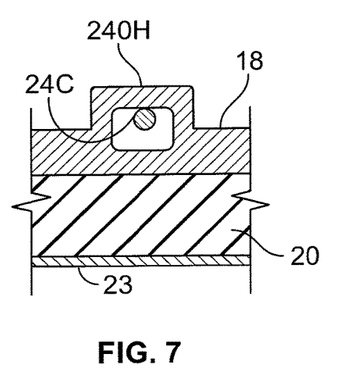
FIG. 7 is a sectional view of one of the padded shells taken along line 7-7 of FIG. 5.

Referring to FIGS. 5-7, the general scheme for guiding cords is illustrated for a specific cord interval over a specific shell, but this scheme is typical of how cords are to be guided for all the shells. In this illustrated case, dorsal shell 18 has a channel 238J that is open on top (i.e., an open topside) and is bordered on opposite sides by a parallel pair of walls 238J-1 Channel 238J communicates on its right with underpass 240H, which is closed on top and open on the bottom (i.e., an open underside). Channel 238J and underpass 240H are integral with and made of the same material as shell 18. The opposite end of channel 238J communicates with underpass 240G, which is structured similarly to underpass 240H. Underpass 240G in turn communicates with relatively short channel 238I. The distal end of channel 238I communicates with gutter 242C, which runs to the edge of dorsal shell 18.

Cord segment 24C is shown in phantom routed under underpass 240H, and between walls 238J-1 of channel 238J. From there cord 24C travels under underpass 240G, and through channel 238I and gutter 242C. Cord 24C is shown exiting from gutter 242C and passing over wall 21 of pad 20.

The inner surface of pad 20 is fitted with a sheet of hook and loop fastening material 23 that is glued in place.

Figure 8:
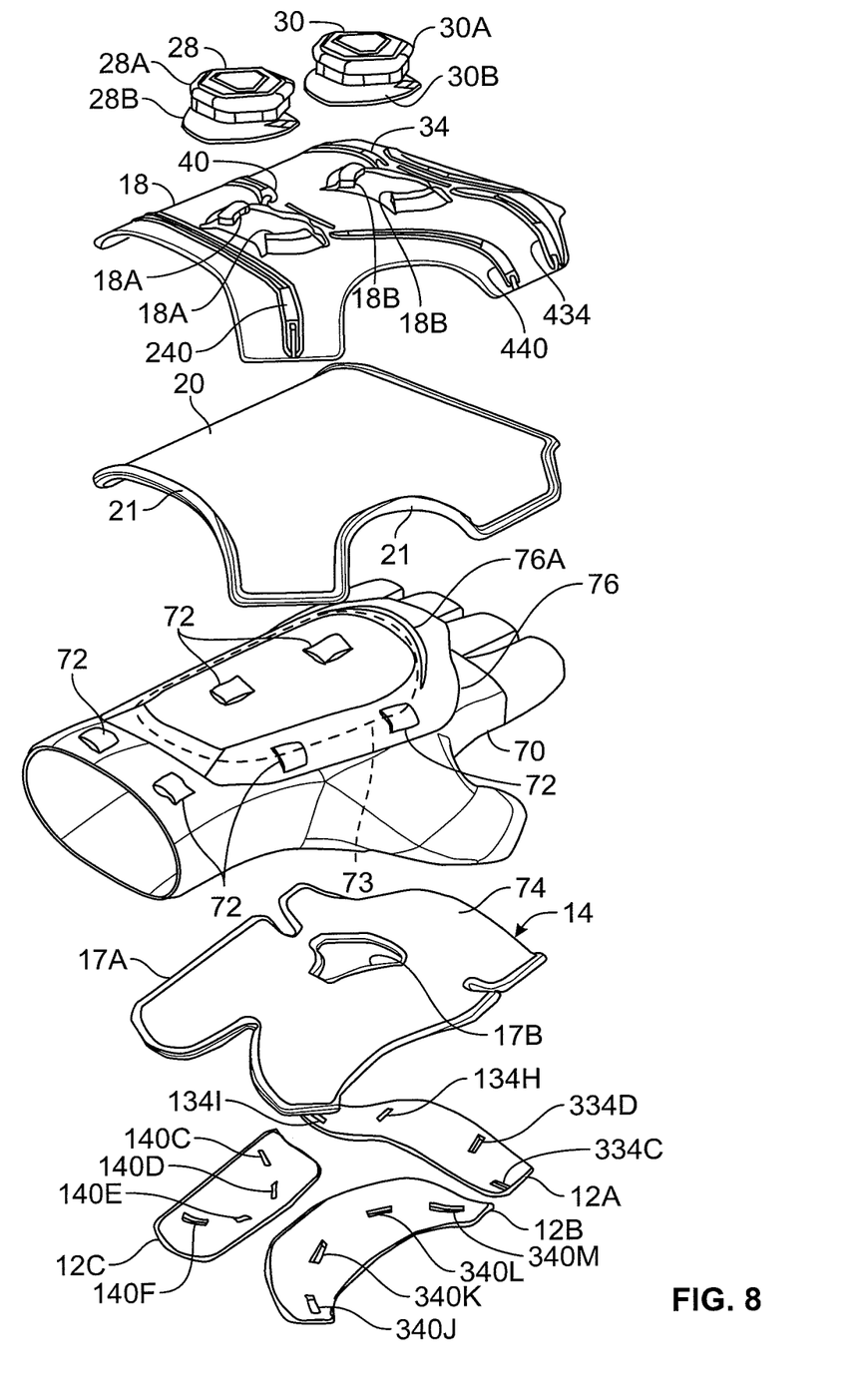
FIG. 8 is an exploded view of the compression device of FIGS. 1 and 2.

Referring to FIG. 8, winder 28 (30) is shown with a knob 28A (30A) rotatably mounted on body 28B (30B). Body 28B will be held in cantilevered clips 18A, while body 30B will be held in cantilevered clips 18B. Clips 18A and 18B are molded into shell panel 18.

As previously mentioned, dorsal shell 18 will be glued in place on pad 20 between walls 21. Likewise, volar shells 12A, 12B, 12C will be glued in place on inside pad 74 between walls 17A and 17B. Satisfactory results will be achieved with urethane based adhesives, both spray and liquid form, although other adhesives are contemplated as well.

Compression glove 70 is shown with five receptacles for the thumb and the four other fingers. Glove 70 fitted on both sides with a number of hook and loop fasteners 72, six being visible on the dorsal side of the glove in this view. A similar number of fasteners are fitted on the volar side of glove 70.

Fasteners 72 will attach to a sheet of hook and loop fastening material glued to the underside of inside pad 20 (hook and loop sheet not visible in this view). The inwardly facing side of previously mentioned inside pad 14 is fitted with a sheet 74 of hook and loop fastening material, which allows attachment to complementary fasteners 72 on the volar side of glove 70.

Glove 70 has pockets on the dorsal and volar sides, dorsal pocket 76 being visible in this view. Pocket 76 has an opening 76A through which one can insert an inside foam pad 73. Foam pad 73 is closer to the skin than pad 20 and will be made out of a softer material to increase comfort. The same can be said for the pad on the volar side of glove 70.

It is desirable that the stored pair of inside pads in the glove pockets be more compliant than pads 14 and 20 to add to the wearer's comfort. Also, a softer material will tend to feather the compression forces near the edges of the device, thereby avoiding the tendency to apply undesired lateral compression. Open cell foam material has been found satisfactory for this purpose, although other types of resilient materials can be used as well. An acceptable open cell foam material is available from Canal Rubber Supply Co. of New York (light to medium density). In this embodiment the pocketed foam is ½ inch thick (1.3 cm), but the thickness may be varied, and will typically remain within a range of ¼ to ¾ inch (0.6 to 1.9 cm), with the thickness chosen to accommodate the needs of the patient.

Inside pads 14 and 20 (also referred to as an intervening pair of inside pads) will be a relatively stiffer material designed to transmit forces normal to their surfaces. Satisfactory results will be achieved when pads 14 and 20 are made from molded foam (PE, PU, EVA, etc.) or cast urethane, although other materials are contemplated as well.

Figure 9:
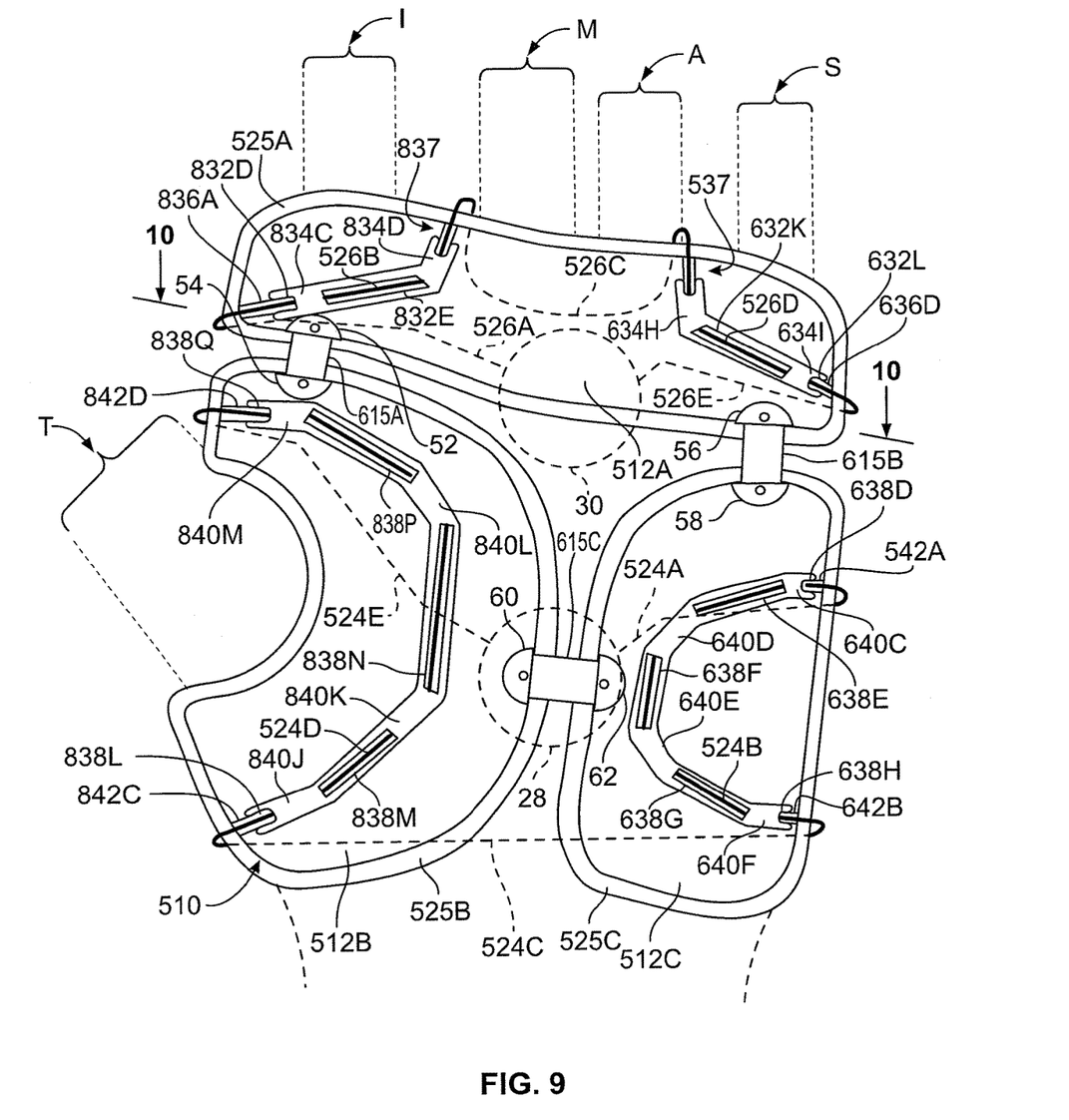
FIG. 9 is an outside view of a trio of volar shells that is an alternate to that of FIG. 2.
Figure 10:
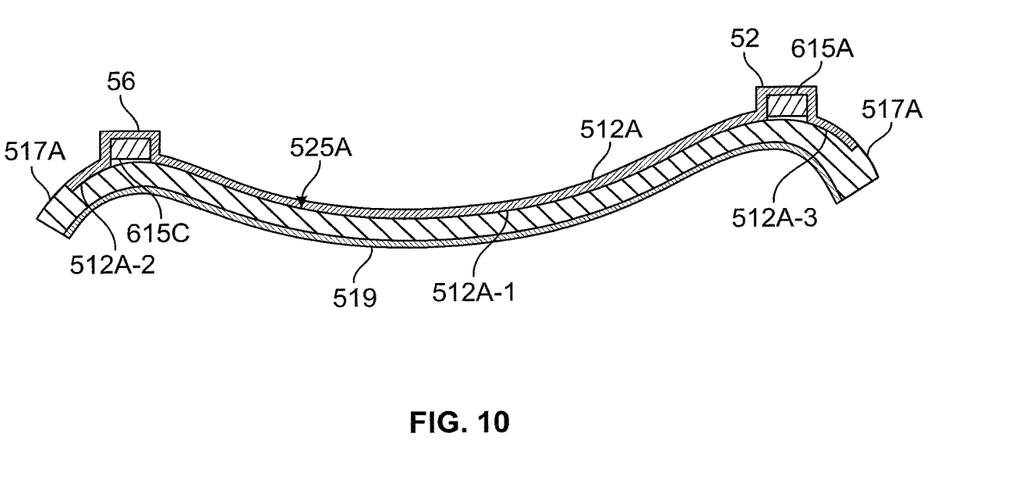
FIG. 10 is a sectional view of one of the padded shells taken along line 10-10 of FIG. 9.

Referring to FIGS. 9 and 10, an alternate volar shell arrangement has a shell structure 510 including transverse shell 512A, medial shell 512B, and lateral shell 512C Components corresponding to those previously illustrated in connection with FIG. 2 have the same reference numerals but increased by 500. In particular, cord segments 524B, 524D, 526B, and 526D are threaded through overpasses and channels that are essentially the same as those previously illustrated in FIG. 2. Volar shell structure 510 will cooperate with the dorsal shell arrangement shown in FIG. 1.

This embodiment differs in that the previously mentioned inside pad of FIG. 3, has been replaced with three discrete inside pads 525A, 525B, and 525C arranged to hold shells 512A, 512B, and 512C, respectively. Pads 525A, 525B, and 525C each have peripheral walls whose inside perimeters match the outlines of shells 512A, 512B, and 512C, respectively. Shells 510A, 510B, and 510C are interconnected by flexibles splines 615A, 615B, and 615C which act as coupling devices.

First spline 615A connects between semicylindrical hood (concavity) 52 on shell 512A and semicylindrical concavity 54 on shell 512B. Second spline 615B connects between semicylindrical hood (concavity) 56 on shell 512A and semicylindrical concavity 58 on shell 512C. Third spline 615C connects between semicylindrical hood (concavity) 60 on shell 512B and semicylindrical concavity 62 on shell 512C. Splines 615A, 615B, and 615C may be riveted on either end to concavities 52-62.

As before, flexible splines 615A, 615B, and 6150 allow articulation between shells 512A, 512B, and 512C. Splines 615A, 615B, and 615C may be made of material similar to that of pads 525A, 525B, and 525C.

In FIG. 10 previously mentioned concavities 52 and 56 are shown containing splines 615A and 615C. Pad 525A has wall 517A bordering transverse shell 512A. The inner face of pad 525A is fitted with a sheet of hook and loop fastener material 519, which is glued in place. The layered arrangement of pad 525A is typical of that found in pads 525B and 525C.

The inside face of shell 512A has a convex underside in medial region 512A-1, and a concave underside in outer regions 512A-2 and 512A-3. The curvature of medial region 512A-1 tends to cup the hand around metacarpo-phalangeal joints of four fingers, excluding the thumb.

Figure 11:
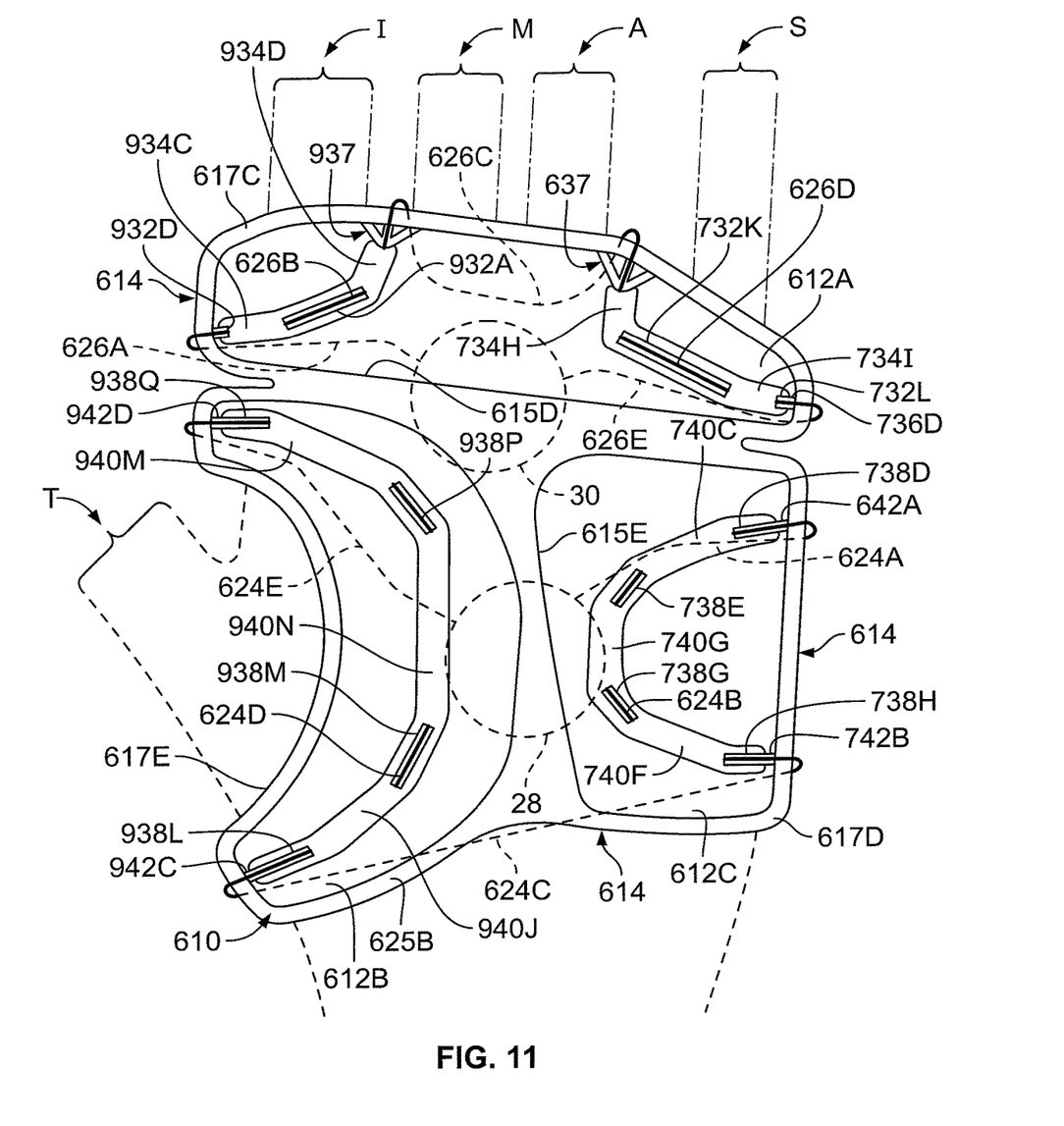
FIG. 11 is an outside view of a trio of volar shells that is an alternate to that of FIGS. 2 and 9.

Referring to FIG. 11, an alternate volar shell arrangement has a shell structure 610 including transverse shell 612A, medial shell 612B, and lateral shell 612C. Components corresponding to those previously illustrated in connection with FIG. 2 have the same reference numerals but increased by 600. Volar shell structure 610 will cooperate with the dorsal shell arrangement shown in FIG. 1.

Volar panels 612A, 612B, and 612C are interconnected by means of inside pad 614, specifically by its bridges 615D and 615E, acting as coupling devices. (Previously described wall 17B of FIG. 2 is supplanted by bridges 615D and 615E.) Inside pad 614 is shown as a collection of three pad regions, sized to receive shell panels 612A, 612B, and 612C.

Transverse shell 612A is bordered on its proximal side by transverse bridge 615D and on the remaining sides by wall 617C. Shell 612B is bordered medially by bridge 615E, on the distal side by bridge 615D, and on the outer and proximal sides by wall 617E. Shell 612C is bordered medially by bridge 615E, on the distal side by bridge 615D, and on the lateral and proximal sides by wall 617D.

Flexible bridges 615D and 615E allow shells 612A, 612B, and 612C to articulate relative to each other. Specifically, flexible bridge 615D allows shell 612A to articulate relative to shells 612B and 612C. Also, flexible bridge 615E allows relative articulation between shells 612B and 612C.

Cord segments 624B, 624D, 626B, and 626D are threaded through overpasses and channels that are essentially the same as those previously illustrated in FIG. 2, except channels 138F and 338P have been eliminated and replaced with underpasses 740G and 940N, respectively. Underpass 740G runs directly between channels 738E and 738G, while underpass 940N runs directly between channels 938P and 938M.

Referring now to panel 612B, the medial portion of that panel slopes down into the palm to achieve an intimate fit. The distal and proximal sections of panel 612B also slope down (concave underside) to wrap partially around the metacarpal bone of the forefinger and thumb, respectively.

Transverse panel 612A has shape similar to panel 512A of FIG. 10. Specifically, the inside face of shell 612A has a convex underside in its medial region, and a concave underside in its outer regions.

The arrangement of FIG. 11 offers several advantages. First, panels 612A, 612B, and 612C cover a greater percentage of the volar region. In particular, the medial/distal corner of panel 612C intrudes further into this region. Also, panel 612C is curved about a longitudinal axis to accommodate the lateral edge of the hand and to bring the medial edge and the medial/distal corner of the panel deep into the palm. The radius of curvature of panel 612C is tailored to accommodate a typical anatomy. In order to achieve a good fit, the medial edge of panel 612C is made with a somewhat reduced radius of curvature.

Also, the medial edge of panel 612C is obliquely skewed from the longitudinal axis. This skewing can be in the range of 5° to 20° (in this Figure the skewing is approximately 12° counterclockwise). This skewing accommodates the normal anatomical flexing of the thumb's metacarpal bone.

While the devices of FIGS. 1-11 are mentioned for treating a hand, they can adapted to treat to different body parts such as the foot, forearm, upper arm, calf, or thigh.

To facilitate an understanding of the principles associated with the foregoing apparatus, its operation will be briefly described in connection with the embodiment of FIGS. 1-8. In this embodiment two compression zones are achieved by using two tensioners 28 and 30 and two independent circuits 24 and 26. In the disclosed embodiment, circuit 24 is arranged with four crossovers: two between shells 18 and 12B, and two between shells 18 and 12C.

For circuit 26, the compression affects primarily the knuckles at the base of the fingers (metacarpophalangeal joints). Specifically, the crossover between courses 26A and 26B applies pressure on the medial side of the knuckle for forefinger I. The crossover between courses 26B and 26C applies pressure at the gap between fingers I and M. The crossover between courses 26C and 26D applies pressure at the gap between fingers A and S. The crossover between courses 26D and 26E applies pressure on the lateral side of the knuckle for finger S.

As noted previously one can select one of the trio of paths for each of the triple gutters 37, 137, 237 and 337 to produce the most comfortable fit.

For circuit 24, compression affects the portion of the hand spaced proximally from circuit 26. Specifically, the crossover between courses 24A and 24B applies pressure on the lateral side of the hand about midway between the fingers and wrist. The crossover between courses 24B and 24C applies pressure on the lateral (pinky) side of the hand at a position that is fairly close to the wrist. The crossover between courses 24C and 24D applies pressure on the medial (thumb) side of the hand between the thumb T and wrist. The crossover between courses 24D and 24E applies pressure on the medial (thumb) side of the palm about midway between thumb T and forefinger I.

Winders 28 and 30 can be independently adjusted to establish the compression forces at their respective regions. By tightening (loosening) circuit 26 compression forces can be increased (reduced) around the knuckles at the base of the fingers. The sinuous shape of transverse shell 12A will tend to flatten the adjacent knuckles to reduce cupping and avoid unnecessary stress at this region.

By tightening (loosening) circuit 24 compression forces can be increased (reduced) around the portion of the hand between the wrist and the knuckles at the base of the fingers. At this point the adjacent edges of shells 12B and 12C curve into the palm to accommodate the natural curvature and cupping there.

Since panels 18, 12A, 12B, and 12C are relatively stiff, the forces applied by these panels are substantially perpendicular to the volar and dorsal surfaces of the hand, so that the hand is not squeezed laterally. Pads inside the pockets of glove 70 will usually be a softer material to increase comfort and to provide feathering of compression forces near the edges of shells 12A, 12B, 12C, and 18.

The compression forces produced by circuits 24 and 26 will be initially set by a professional the first time the device is placed on the hand. However, the wearer will be instructed on how to independently don the device without professional assistance. Thereafter, the patient can wear the device during the time periods recommended by the therapist.

To don the device, the patient will put glove 70 on the affected hand in the usual fashion. Then, winders 28 and 30 will be operated to fully slacken circuits 24 and 26. A patient can then slip the gloved fingers between shell structure 16 on the dorsal side, and shell structures 10 on the volar side. When the hand is positioned as shown in FIGS. 1 and 2, winders 28 and 30 can be adjusted to produce the tension in circuits 24 and 26 as demonstrated and recommended by a therapist.

During the course of a day, a patient may find it necessary to increase or decrease the compression forces. Since winders 28 and 30 are easily adjusted, these compression forces can be easily changed by the patient.

The device is easily removed by using winders 28 and 30 to remove all tension on circuits 24 and 26. Thereafter, the gloved hand is withdrawn in a direction opposite to the direction used to don the device, before removing glove 70 Accordingly, the patient can temporarily remove the device for routine activities such as bathing.

When the device is worn, the compression forces will tend to reduce the patient's edema. The compression forces will tend to urge edematous fluids in a proximal direction. At the same time, the patient's fingers, thumb, and wrist will remain highly mobile. Thus, the patient can perform most daily activities. Accordingly, the fingers, thumb, and wrist will be routinely exercising, which will produce a natural pumping effect that tends to reduce edema. In addition, the device is relatively open so that air can reach the hand, which will enhance comfort and avoid elevated temperatures.

The patient will still need to periodically visit a therapist to check the progress and to perform different types of CDT. At these visits the therapist can inspect the condition of the body part, and recommend any changes in regime deemed necessary.

The advantages of this device are: time savings and ease of application, comfort, safety, and therapeutic efficacy. Using appropriate materials and an effective tensioning system, this device offers a high working, low resting pressure environment similar to that which his offered to lymphedema patients during CDT using short stretch (non-elastic) bandaging materials. Furthermore compression is achieved while avoiding trauma to the lymphatic, hemodynamic and neurological system, by using customizable thermoplastics and padding to areas like the hand, forearm, upper arm, calf, thigh and other body parts.

It will be appreciated that various modifications may be implemented with respect to the above described embodiments. In some cases a variety of shells may be manufactured in sizes and shapes designed to accommodate any one of a variety of affected body parts. Also, different sizes can be offered to accommodate patients of different weights, statures, ages, etc. In some embodiments shells may be provided with a large number of alternate channels, overpasses, eyes or lacing hooks, so that the therapist can effectively route a tensioning cord through almost any desired route by selecting different guide elements. In some cases the ligature network will be formed of a single cord but will be segregated into different independent sections by tying some intermediate point on the cord to an anchor, so that tension is not transferred from one section to the other. In some embodiments a pad may be a single layer or may employ more than two layers. Also, instead of installing the softer pads in glove pockets, these pads may be attached to the stiffer pads underlying the plastic shells. In such cases the glove may be eliminated.

Obviously, many modifications and variations of the present invention are possible in light of the above teachings. It is therefore to be understood that within the scope of the appended claims, the invention may be practiced otherwise than as specifically described.

The invention claimed is:

1. A compression device for treating edema, composing:
a plurality of shell structures;
a plurality of inside pads underlying said plurality of shell structures; and
a ligature network routed across said plurality of shell structures, said network inducing:
a plurality of tensioners mounted on at least some of said plurality of shell structures, said plurality of tensioners being operable to separately adjust tension in deferent portions or said ligature network, at least some of said plurality of shell structures having at least one underpass sized to accommodate passage of a portion of said ligature network, said at least one underpass comprising a plurality of underpasses distributed on each of said plurality of shell structures, said plurality of underpasses being integral with, and being formed of the same material as, corresponding ones of said plurality of shell structures, said plurality of underpasses each having an open underside, at least some of said plurality of shell structures having at least one channel extending between an adjacent pair of said plurality of underpasses, said at least one channel being sized to guide a portion of said ligature network, said at least one channel being integral with a corresponding one of said plurality shell structures, said at least one channel comprising a plurality of channels distributed on each of said plurality of shell structures, said plurality of channels being internal with, and being formed of the same material as, corresponding ones of said plurality of shell structures, each of said plurality of channels extending between a different corresponding pair of a plurality of adjacent pairs of said plurality of underpasses, said plurality of channels being sized to guide portions of said ligature network.

2. A compression device according to claim 1 wherein said plurality of channels each have a parallel par of watts, and an open topside.

3. A compression device according to claim 1 wherein said device is adapted to treat edema between a longitudinally spaced pair of joints on a body part, said plurality of shell structures each hawing a length sized to avoid restricting articulation of said longitudinally spaced pair of joints.

4. A compression device according to claim 1 wherein at least some of said plurality of shell structures have at least one gutter extending from at least one of said plurality of underpasses for guiding a portion of said ligature network off one of the plurality of shell structures.

5. A compression device according to claim 4 wherein said at least one gutter comprises a diverging plurality of gutters extending torn one of said plurality of underpasses for providing alternate paths for said ligature network.

6. A compression device according to claim 1 wherein one of said plurality of shell structures comprises:
   a plurality of panels having at least one coupling device connecting together a coupled pair of said plurality of panels.

7. A compression device according to claim 6 wherein said coupled pair each have a concavity for receiving opposite ends of the at least one coupling device.

8. A compression device according to claim 1 wherein one of said plurality of shell structures comprises:
   a plurality of panels, a predetermined set of said plurality of inside pads underlying said plurality of panels, said compression device comprising:
   one or more bridges connecting together said predetermined set of said plurality of inside pads.

9. A compression device according to claim 1 wherein said ligature network includes a cord, said plurality of tensioners each composing:
   a manually operable winder for winding said cord.

10. A compression device accenting to claim 1 comprising:
    a glove mounted between an opposing pair of said plurality of shell structures.

11. A compression device according to claim 10 wherein said glove has a pocket, one of said plurality of inside pads being held to said pocket.

12. A compression device according to claim 10 wherein said sieve has a dorsal pocket and a volar pocket, a stored pair of said plurality of inside pads being separately held in said dorsal and said volar pockets.

13. A compression device according to claim 12 wherein an intervening pair of said plurality of inside pads is mounted between said opposing pair of said plurality of shell structures, and on opposite sides of said glove.

14. A compression device according to claim 13 wherein said stored pair of said plurality of inside pads each comprises:
    a open cell foam material.

15. A compression device for treating edema according to claim 1, comprising:
    one of said plurality of shell structures comprising:
    a plurality of panels having at least one coupling device connecting together at toast a coupled pair of said plurality of panels.

16. A compression device according to claim 15 wherein said coupling device comprises at least one flexible spine, said coupled pair each having a concavity far receiving opposite ends of the at least one spine.

17. A compression device according to claim 15 wherein said coupling device comprises:
    a substrate underlying said coupled pair.

18. A compression device according to claim 17 wherein said substrate comprises a pair of strata interconnected by at least one flexible bridge, said bridge extending between said coupled pair.

19. A compression device according to claim 1 wherein said plurality of shell structures include a dorsal shell and an adjacent plurality of volar shells.

20. A compression device according to claim 19 wherein said plurality of volar shells are mutual spaced and comprise:
    a transverse volar shell;
    a medial volar shell; and
    a lateral volar shell.

21. A compression device according to claim 20 wherein said transverse volar shelf has an inside surface with a convex central interval.

22. A compression device according to claim 21 wherein adjoining portions of said medial volar shell and said lateral volar shell are curved inwardly toward said dorsal shell.

23. A compression device according to claim 21 comprising a coupling device for connecting together said plurality of volar shell structures.

24. A compression device according to claim 23 said coupling device comprises:
    a first flexible spine connected between said transverse shell and said medial volar shell;
    a second flexible spline connected between said transverse shell and said lateral volar shell; and
    a third flexible spine connected between said medial volar shell and said lateral volar shell.

25. A compression device according to claim 23 wherein said coupling device comprises:
    a substrate underlying said plurality of volar shell structures, said substrate having a trio of regions interconnected by a plurality of flexible bridges extending between corresponding pairs of said plurality of volar shell structures.

26. A compression device according to claim 23 wherein said plurality of tensioners are located on said dorsal shelf.

27. A compression device according to claim 21 wherein said medial volar shell has a curved notch steed to provide clearance for a human thumb.

28. A compression device according to claim 27 comprising:
    a compression glove located between said dorsal shell and said plurality of volar shells, said glove having a thumb receptacle aligned with said curved notch.

29. A compression device according to claim 28 comprising:
    a hook and loop type fastener mounted upon said glove for fastening to at least some of said plurality of shell structures.

30. A compression device according to claim 28 wherein said compression glove includes an open cell foam material.

31. A compression device according to claim 21 wherein said ligature network includes a cord, said plurality of tensioners each comprising:
    a manually operable winder for wincing said cord.

32. A compression device according to claim 20 wherein said transverse volar shell has an inside surface with a transversely spaced pair of concave intervals on either side of a convex central interval.

33. A compression device according to claim 32 wherein said transverse volar shell has a transverse proximal edge, said medal volar shell and said lateral volar shell being located on the same side of said transverse proximal edge.

* * * * *